United States Patent
Burt et al.

(10) Patent No.: US 10,363,436 B2
(45) Date of Patent: Jul. 30, 2019

(54) RADIOTHERAPY APPARATUS USING INERTIAL CHARACTERISTICS FOR DELIVERY PLANNING

(71) Applicant: Elekta AB (publ), Stockholm (SE)

(72) Inventors: David Burt, West Sussex (GB); Paul Boxall, West Sussex (GB)

(73) Assignee: ELEKTA AG (PUBL), Stockholm (SE)

(*) Notice: Subject to any disclaimer, the term of this patent is extended or adjusted under 35 U.S.C. 154(b) by 307 days.

(21) Appl. No.: 14/652,085

(22) PCT Filed: Dec. 14, 2012

(86) PCT No.: PCT/EP2012/075622
§ 371 (c)(1),
(2) Date: Jun. 12, 2015

(87) PCT Pub. No.: WO2014/090336
PCT Pub. Date: Jun. 19, 2014

(65) Prior Publication Data
US 2015/0314139 A1    Nov. 5, 2015

(51) Int. Cl.
*A61N 5/10*    (2006.01)

(52) U.S. Cl.
CPC ........... *A61N 5/1048* (2013.01); *A61N 5/103* (2013.01); *A61N 5/1067* (2013.01); *A61N 5/1071* (2013.01); *A61N 5/1081* (2013.01)

(58) Field of Classification Search
CPC .... A61N 5/103; A61N 5/1037; A61N 5/1048; A61N 5/1071; A61N 5/1081; A61N 5/1067; A61N 5/10; A61B 2018/00666
See application file for complete search history.

(56) References Cited

U.S. PATENT DOCUMENTS

| | | | |
|---|---|---|---|
| 6,999,556 B2* | 2/2006 | Nakano | A61N 5/103 378/152 |
| 2008/0144772 A1* | 6/2008 | Yi | A61N 5/1049 378/65 |

(Continued)

FOREIGN PATENT DOCUMENTS

| | | |
|---|---|---|
| EP | 0314214 A2 | 5/1989 |
| WO | WO 02/49044 A2 | 6/2002 |
| WO | WO 2009/052845 A1 | 4/2009 |

OTHER PUBLICATIONS

International Search Report and Written Opinion in International Application PCT/EP2012/075622, dated Apr. 15, 2013.

*Primary Examiner* — Brooke Purinton
(74) *Attorney, Agent, or Firm* — Finnegan, Henderson, Farabow, Garrett & Dunner, L.L.P.

(57) ABSTRACT

A method for dealing with the effects of inertia in a radiotherapy apparatus is disclosed. The method may include catering for inertia in advance by incorporating inertia factors into an output from a delivery control system which adapts the treatment plan by incorporating the inertia factors, or by including the inertia factors as a constraint in the treatment planning process. The instructions delivered to the geometry items may reflect their inertia behavior and can therefore be followed very closely. This may indicate that a departure from that plan will be correspondingly more likely to indicate an error by the geometry item. When a geometry item needs to accelerate or decelerate, less error may arise and thus the error-checking regime may not necessarily make allowances for such departures from the intended path, thereby tightening the error tolerances. Error-checking may be safely carried out locally for each component.

10 Claims, 8 Drawing Sheets

(56) References Cited

U.S. PATENT DOCUMENTS

| | | | |
|---|---|---|---|
| 2008/0187097 A1* | 8/2008 | Cheng | A61N 5/107 378/65 |
| 2008/0232664 A1* | 9/2008 | Nagamine | A61N 5/1048 382/131 |
| 2009/0003975 A1* | 1/2009 | Kuduvalli | A61N 5/1049 414/146 |
| 2009/0121155 A1 | 5/2009 | Brown et al. | |
| 2010/0303205 A1 | 12/2010 | Kapoor et al. | |
| 2010/0329422 A1* | 12/2010 | Brown | A61N 5/103 378/65 |
| 2012/0004518 A1 | 1/2012 | D'Souza et al. | |

* cited by examiner

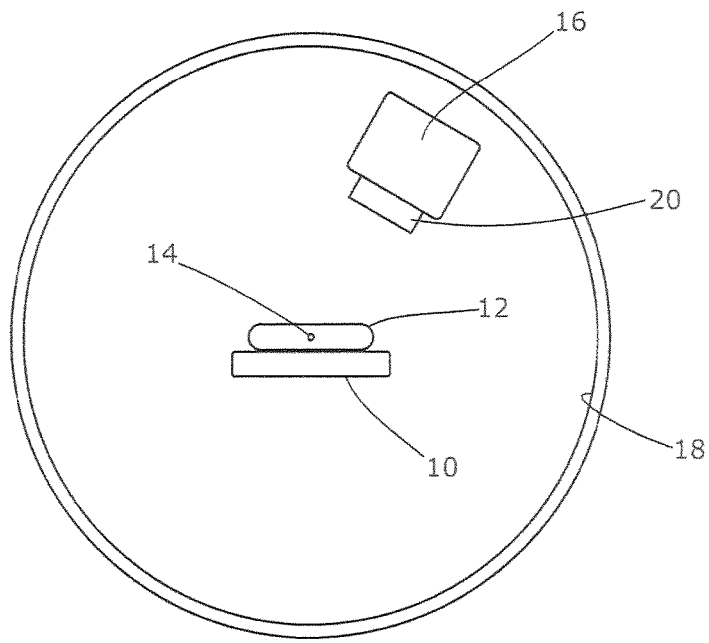
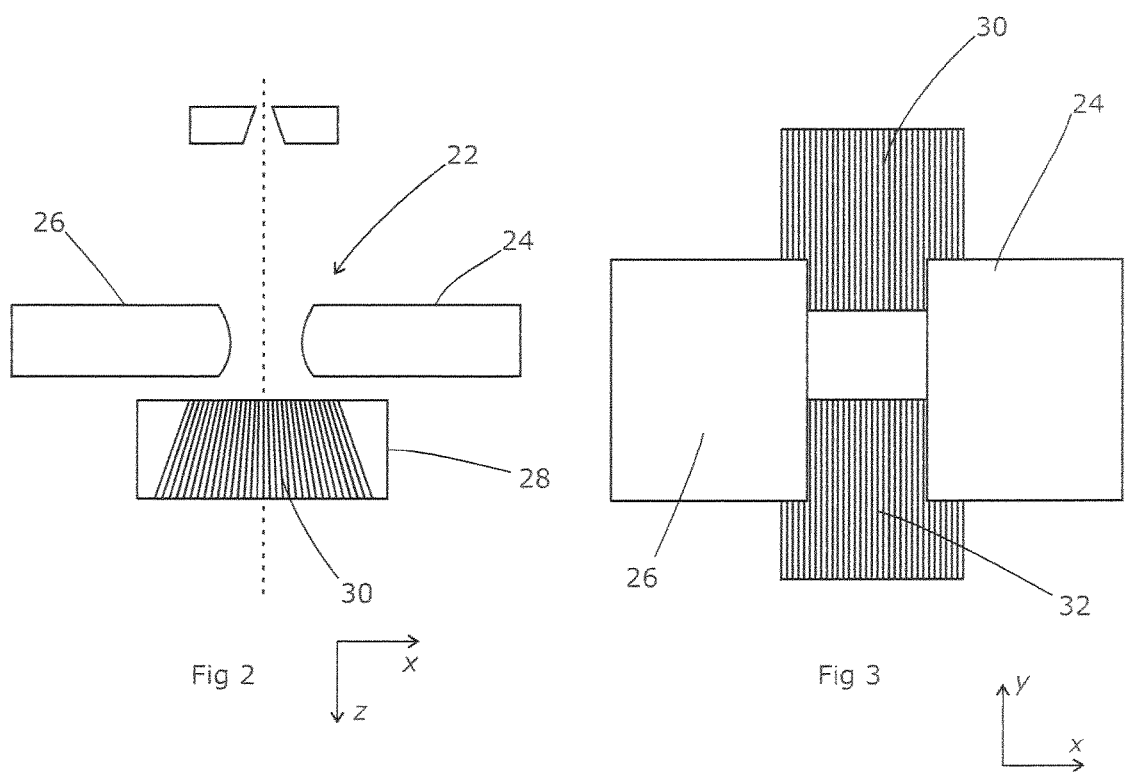

RADIOTHERAPY APPARATUS USING INERTIAL CHARACTERISTICS FOR DELIVERY PLANNING

CROSS REFERENCE TO RELATED PATENT APPLICATION

This application is a national phase of International Application No. PCT/EP2012/075622, filed on Dec. 14, 2012, the entire content of which is incorporated herein by reference.

FIELD OF THE INVENTION

The present invention relates to apparatus for radiotherapy.

BACKGROUND ART

Radiotherapy is a process whereby a beam of harmful radiation is directed generally towards a region of a patient, usually in order to treat a tumour within that region. The radiation causes damage to living cells in its path, and hence inhibits or reduces the tumour. It also damages healthy tissue if applied in significant doses, and therefore efforts are made to limit the dose to healthy tissues while maintaining the prescribed dose to cancerous tissue.

One apparently straightforward means of limiting the dose to healthy tissue is to direct the beam towards the tumour from a plurality of different directions. Thus, the total dose delivered to the tumour can be significantly greater than the dose applied to any individual section of surrounding tissue. A common approach to doing so is to mount the radiation source on a rotatable support, with the source being oriented towards the rotation axis of the support so that the beam intersects with the axis. Thus, as the support rotates, the beam always passes through the point of intersection (usually referred to as the "isocentre") but does so from every radial direction around the isocentre. This requires the support to be rotated around the patient; the support has a significant mass and therefore the engineering challenge that this presents is significant.

Another means of limiting the dose applied to healthy tissue is the so-called "multi-leaf collimator" or "MLC" as shown in, for example, EP-A-314,214. An plurality of long narrow leaves are arranged side-by side in an array, and are individually controllable via a servo-motor so that they can each be extended or retracted by a desired amount. Thus, by moving individual leaves, a collimator can be made to a desired shape. A pair of such collimators, one either side of the beam, allows the beam to be shaped as desired thereby allowing healthy tissue to be placed in shadow.

In a multi-leaf collimator, the leaves are generally thin in the direction transverse to the direction of movement, to provide a good resolution, and long in the direction of movement so as to provide a good range of movement. In the direction of the beam, the leaves need to be relatively deep; even when made of a high atomic number material such as Tungsten, such depth is required in order to offer an adequate attenuation of the beam. Thus, leaves are relatively heavy and difficult to move.

Both of these aspects of a radiotherapy apparatus require the relevant geometry item (in this case the rotatable support and the MLC leaves) to be moved during treatment in an accurate manner. Older "step and shoot" methods called for the geometry item to be moved to a specific location, which can be checked easily by known servo-control methods. However, to improve treatment times, more modern treatment control methods call for the geometry item to be moved at a specific (linear or rotational) speed over a specific time period, after which it is moved at a (potentially) different speed for a further time period. This raises the issue of inertia.

Specifically, a conventional treatment plan might (for example) call for the geometry item to move at a particular speed $v_1$ over a time period $t_1$ followed by a speed $v_2$ over a subsequent time period $t_2$. The geometry items cannot and will not change their speed immediately, there will in practice be a catch-up period during which the actual speed will be incorrect, either too high if $v_1 > v_2$ or too low if $v_1 < v_2$. In either case, the geometry item will be at an incorrect location during delivery of at least part of the dose. Our earlier application US 2009-121155-A1 therefore provided a radiotherapeutic apparatus comprising a geometry item that was moveable to adjust the geometry of the beam, and a control unit being arranged to cause variations in the speed of movement of the geometry item and also adjust the dose rate of the radiation source for a period of time after a change in the speed of the geometry item. This sought to compensate for the effects of inertia by restraining the dose rate temporarily, under local control.

SUMMARY OF THE INVENTION

We have found a superior approach for dealing with the effects of inertia. This approach also has beneficial consequences for the error-checking systems of the apparatus, which (in turn) has beneficial consequences for the system control architecture.

Specifically, whereas the approach of US2009121155A1 was to deal with inertia locally, by temporarily adjusting the dose rate in order to compensate for a geometry item that was not up to speed or still travelling too quickly, we now propose to cater for inertia in advance by incorporating inertia factors into the delivery planning process. This can be achieved in either of two ways. Preferably, after the treatment plan has been produced, it will be processed by a delivery control system that will incorporate the effects of inertia on the geometry items and produce a set of instructions for the machine to implement which reflect the inertia behaviour of the geometry items and can therefore be followed very closely. Alternatively, instead of producing a treatment plan that assumes perfect inertia-less behaviour by the geometry item and then compensating for this afterwards, the treatment plan can comprise a set of instructions that reflect the inertia behaviour of the geometry items and can therefore be followed very closely.

This, in turn, means that a departure from that plan will be correspondingly more likely to indicate an error by the geometry item. It will no longer be routine for errors to arise when a geometry item needs to accelerate or decelerate and thus the error-checking regime need not make allowances for such departures from the intended path. That, in turn, means that the error tolerances can be correspondingly tighter.

Those tighter tolerances mean that the error-checking can safely be carried out locally for each component. Wider error tolerances provided in order to encompass normal inertia-led variances leave open the possibility that the apparatus as a whole is non-compliant despite all individual components being compliant if, for example, more than one component is at or near the limit of its error tolerance. In such circumstances, the combined effect of the sub-tolerance errors could take the apparatus as a whole out of tolerance. In such a system, error-checking therefore needs to be centralised, taking into account all the reported component errors so that potentially troublesome combinations can be detected. This creates a significant level of complexity which is avoided entirely by the tighter tolerances enabled by the present invention.

In one aspect, the present invention therefore provides a delivery control system for a radiotherapy apparatus, arranged to transmit a treatment plan for delivering a dose distribution to delivery elements of the radiotherapy apparatus, the delivery control system comprising a processor, at least one data store, and a program stored in the data store, the program being adapted to cause the processor to receive the treatment plan, receive inertial characteristics of the delivery elements, perform a process on the treatment plan in order to produce a delivery plan which corresponds to the treatment plan in the light of the inertial characteristics, and transmit at least part of the delivery plan to the delivery elements. The program can also cause the processor to monitor the delivery elements for conformance to the delivery plan.

The delivery control system can form part of a radiotherapy apparatus, which will further comprise a plurality of delivery items, each with an associated local control unit, the delivery control system being arranged to provide a plurality of sequential delivery instructions from the delivery plan to the local control units and, subsequently, instruct the local control units to commence the treatment, the local control units being adapted to receive the delivery control system instructions and, after receiving the instruction to commence treatment, command movement of the geometry item and monitor subsequent actual movement of the geometry item, compare the actual movement with the movement set out in the delivery control system instructions, and create an alert state if the difference is greater than a threshold, the delivery control system being adapted to cease the treatment if any local control unit is in an alert state.

In a second aspect, the present invention provides a treatment planning computer for creating a treatment plan for delivering a dose distribution via a radiotherapy apparatus that is subject to a plurality of machine constraints, the treatment planning computer comprising a processor, at least one data store, and a program stored in the data store, the program being adapted to cause the processor to receive the dose distribution, receive the machine constraints in a form including at least a geometry of a geometry item of the apparatus, a maximum speed of the geometry item, and a maximum rate of change of speed of the geometry item, and perform an iterative process thereon in order to produce a treatment plan capable of delivering the dose distribution via a radiotherapy apparatus subject to the machine constraints.

Such a treatment planning computer can, for example, produce a treatment plan for use by a radiotherapy apparatus comprising a plurality of geometry items, each with an associated local control unit, the apparatus being arranged to provide a plurality of sequential treatment planning instructions from the treatment plan to the local control units and, subsequently, instruct the local control units to commence the treatment, the local control units being adapted to receive the treatment planning instructions and, after receiving the instruction to commence treatment, command movement of the geometry item and monitor subsequent actual movement of the geometry item, compare the actual movement with the movement set out in the treatment planning instructions, and create an alert state if the difference is greater than a threshold, the apparatus being adapted to cease the treatment if any local control unit is in an alert state. The invention relates to such a radiotherapy apparatus per se, and in combination with the treatment planning computer.

The radiotherapy apparatus may be adapted to continue the treatment provided that no local control unit is in an alert state.

BRIEF DESCRIPTION OF THE DRAWINGS

An embodiment of the present invention will now be described by way of example, with reference to the accompanying figures in which;

FIG. 1 shows a schematic layout of a radiotherapy apparatus;

FIG. 2 shows a schematic vertical section through a beam collimation system for the radiotherapy apparatus of FIG. 1;

FIG. 3 shows a schematic beam's eye view through a beam collimation system for the radiotherapy apparatus of FIG. 1;

DETAILED DESCRIPTION OF THE EMBODIMENTS

Figure 4:
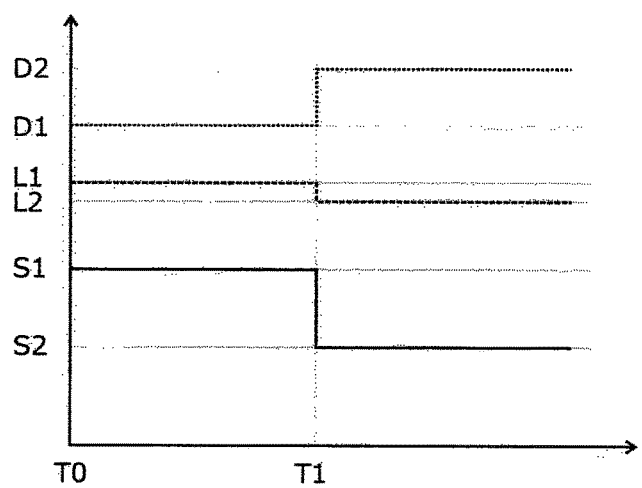
FIG. 4 shows the collimator movements and dose rates planned by a typical known treatment planning computer.

Referring to FIG. 1, a typical radiotherapy apparatus includes a patient table 10 on which can be placed a patient 12. Generally, the patient table is moveable (within limits) in any of its six degrees of freedom, i.e. three translational directions and three rotational directions, so as to place the relevant part of the patient that is to be treated at a specific location 14 within the treatment room, known as the "isocentre". This may be made visible by a number of low-power lasers mounted at fixed locations and directed towards the isocentre 14.

A radiation source 16 is mounted on a gantry (not visible) extending from a rotatable support 18. The radiation source may emit high-energy x-rays, or an electron beam, or a selectable choice of both, or another form of radiation. The rotatable support is usually set into a wall or other structure, so that the operating machinery can be concealed. The support 18 can rotate around a horizontal axis that passes through the isocentre 14, and the source 16 extends from the support 18 at a point offset from that horizontal axis but is directed towards the axis and the isocentre 14. Thus, as the support 18 rotates, the radiation source 16 illuminates the region around the isocentre 14 from all possible radial directions. This provides one way in which the apparatus limits the radiation dose applied to healthy tissue while maintaining the dose applied to the tumour or other lesion being treated; the lesion (or relevant part of it) can be exposed during the entirety of the treatment, but the surrounding tissue will only be exposed when directly in line with the beam.

Another way of limiting the dose applied to healthy tissue is the use of collimators for the radiation beam. These are housed as a collimator set 20 integrated with the radiation source 16 and acting on the beam so as to limit its lateral extent. They are shown schematically in FIGS. 2 and 3, and comprise two pairs of collimators, each acting in mutually transverse directions so as to limit the beam in all directions. Thus, a block collimator 22 comprises a pair of collimating sections 24, 26 which are moveable back and forth in an x direction and have a flat front face substantially parallel with the y direction. By moving the blocks back and forth, the beam can be limited in the x direction as desired.

The second pair of collimators are multi-leaf collimators 28. These comprise two mutually opposed banks 30, 32 of leaves, each leaf being extendable back and forth in the y direction and being relatively long in the y direction so as to allow it to reach across a significant proportion of the beam width, relatively deep in the z direction so as to allow it to attenuate the beam significantly, and relatively narrow in the x direction so as to allow a good resolution. By moving individual leaves to a desired position, each bank of leaves as a whole can present a front edge that takes up substantially any shape.

Between the two collimators, the beam can be delimited to substantially any required shape, with the block collimator defining the lateral extent of the shape in the x direction and the multi-leaf collimator defining the remaining part of the shape. In combination with the rotational movement of the radiation source 16, the collimators allow a complex three-dimensional dose distribution to be built up within the patient, in line with the prescription developed by the patient's clinician. That dose distribution results from multiple beams of different shapes and different directions of arrival which are produced by varying the angle, dose rate, and collimator shapes during treatment, either stepwise or continuously.

To calculate the necessary rotations, dose rates, and collimator shapes that will deliver a desired dose distribution, a "treatment planning computer" is usually employed. This receives the dose distribution, which will normally be a three-dimensional map showing areas which must receive a specified dose of radiation, such as the lesion itself, areas in which the dose should be minimised to the extent possible, and areas where substantially no radiation or less than a specified dose must be delivered, such as sensitive structures including the bowels, optic nerves, spinal cord, and the like. It also receives a set of "machine constraints", which detail the nature of the apparatus including the geometry of the beam and the collimators, maximum dose rates and maximum rotation speeds, etc. An algorithm is then applied to produce a "treatment plan" comprising detailed instructions for the radiotherapy apparatus in terms of required rotation speeds, dose rates, MLC shapes etc and their variation with time. The details of the algorithm are not relevant to the present invention and are known per se; they are discussed in WO2002/049044 by way of example.

A typical treatment plan is show schematically in FIG. 4. Thus, the rotation speed of the gantry (shown by the solid line) is planned to continue from the beginning at a certain speed S1 until a time T1 at which it drops to S2. Meanwhile, the dose rate (dotted line) maintains a certain level D1 until T1, at which point the dose rate rises to D2. The position of a collimator leaf (dashed line) remains at L1 until time T1 at which point it withdraws to L2.

In practice, of course, the treatment plan will be considerably more complex. It will deal with 80 or 160 MLC leaves and may include more variations in the dose rate and the rotation speed. However, FIG. 4 illustrates the principle.

Figure 5:
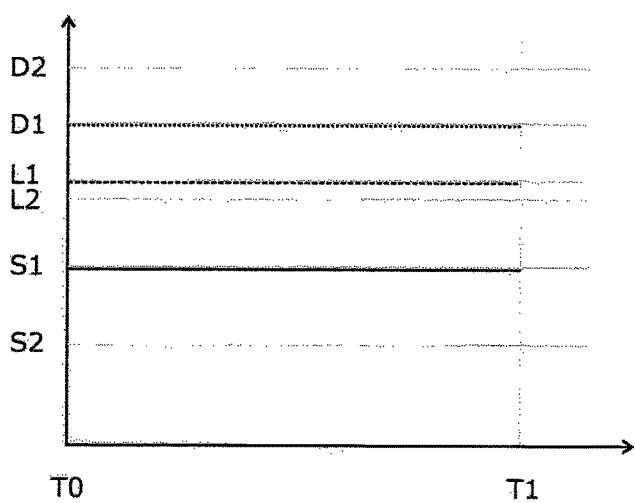
FIG. 5 shows the planned collimator movements and dose rates for an individual delivery step.
Figure 6:
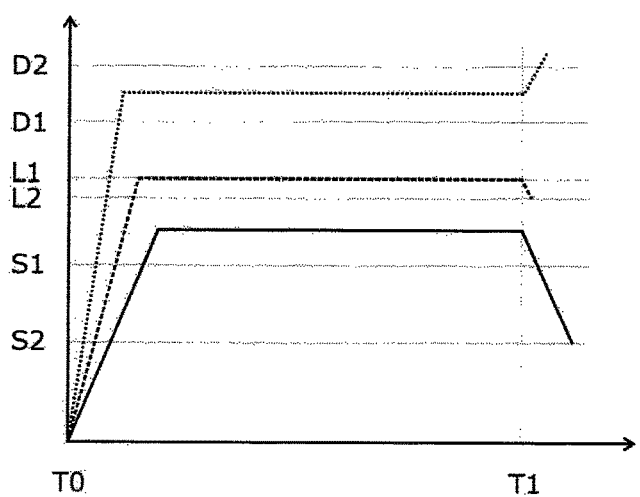
FIG. 6 shows the collimator movements and dose rates typically obtained in practice as a result of the treatment plan of FIG. 4.

In practice, the apparatus does not deliver precisely this plan due to the inertia of the various components. Considering an individual delivery step of the treatment plan (e.g. the period from T0 to T1 in FIG. 4) a specific dose rate D1 (etc) is selected for that delivery step by the treatment planning computer based on the dynamic characteristics of the system. The algorithm employed by the treatment planning computer assumes that the dose rate and velocity of all axes will be constant over the step as shown in FIG. 5. In fact, the outcome that is delivered is shown in FIG. 6; the dose rate takes some time to ramp up to the desired level, and the gantry takes somewhat longer to accelerate to the desired rotation speed. Both are therefore allowed to overshoot their intended levels as set out in US2009121155A1 so that the total dose delivered and the total angle traveled during the delivery step are correct. In addition, there is an initial period during which the collimator is still moving to its set position. It is clear from these diagrams that the possible performance does not closely match that planned. The three phases of each component's travel are not aligned, and therefore tracking performance is not optimal. Additional complexity is introduced into the local control units that initiate and monitor the individual components movements in order to compensate for the inertia by moving faster in the static phase of the delivery step.

This also complicates the error-checking of the system as a whole by the delivery control system. It is difficult to enforce very close error tolerances, for the simple reason that deviations from the treatment plan due to the inertia of the moving parts are inevitable. Therefore, these must be allowed for and an error-checking system that simply compared the intended state of each component with its actual state would regularly issue false positive error reports. Therefore, the system as a whole needs to be considered, to ensure that the delay in moving the collimator is not problematic in the light of the current dose rate and the current gantry position, for example. This will evidently produce a highly complex error-checking system. Given that complex systems are inherently more difficult to validate (and to monitor for errors), this is undesirable.

Figure 7:
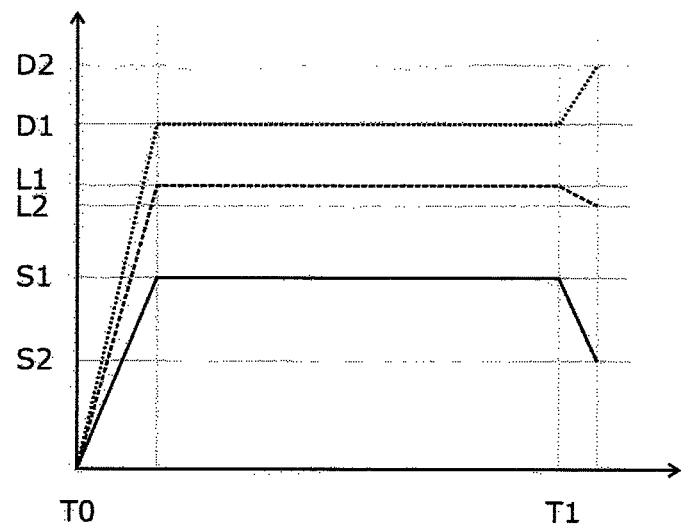
FIG. 7 shows the collimator movements and dose rates proposed according to the present invention.

According to the invention, the dynamic characteristics of all the delivery components of the system are profiled to identify their maximum rate of change (including dose). That dynamic characteristic information is then used to allow matching of the acceleration and deceleration phases of all components, again including dose. This is most easily done by a by a delivery control system 52 (FIG. 8), which receives the treatment plan from the treatment planning computer 50 and adjusts the machine commands contained within the treatment plan to incorporate the dynamic characteristic information. Alternatively, the dynamic characteristic information can be used as a machine constraint within the treatment planning algorithm used by the treatment planning computer 50, to produce a treatment plan that is directly usable without modification. In either case, dose is thus treated as a movement i.e. a specific MU ("monitor unit") is considered in a manner equivalent to position, & MU/min (dose rate) is considered in a manner equivalent to velocity. FIG. 7 shows the result, with the dose rate and the collimator position being changed at a deliberately slower rate so that they all reach their intended position (or rate) at the same time as the slowest item being controlled, in this case the gantry. For other transitions between delivery steps, a different component might be the slowest as although the gantry is particularly heavy and hence subject to inertia, a different transition might require only a small change in the gantry speed but a large change in the dose rate (for example). Thus, all the components affecting the beam geometry (the "geometry items") move in synchrony and no compensation is needed.

Figure 8:
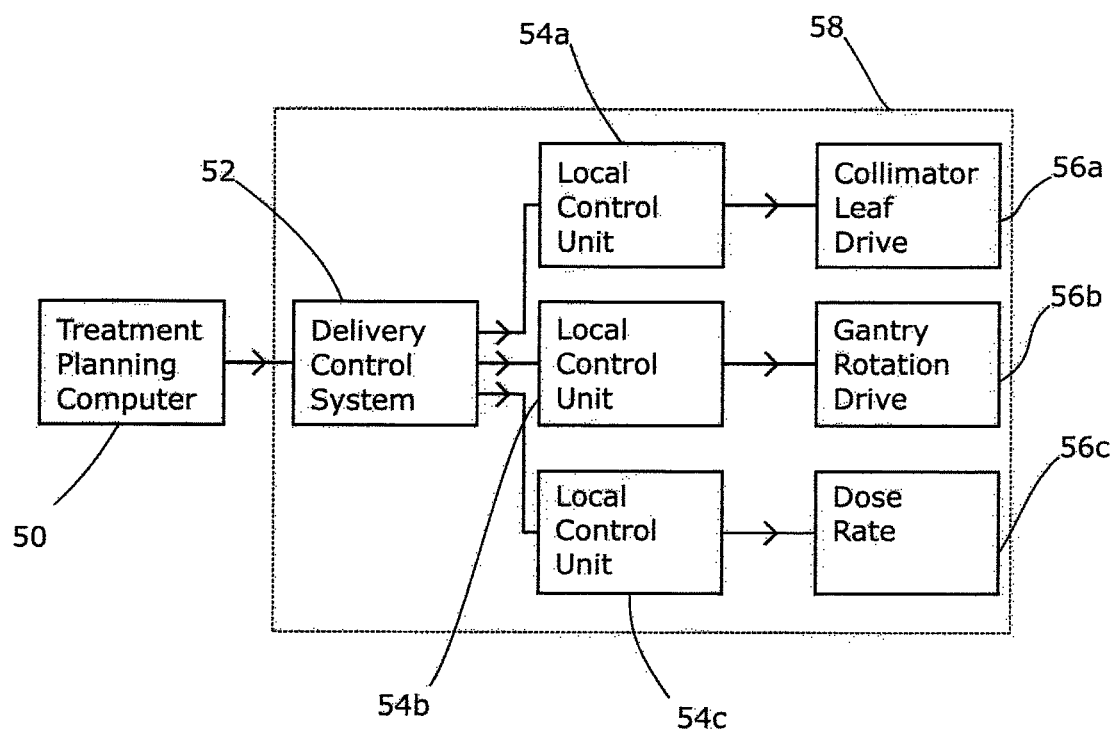
FIG. 8 shows the control arrangements for the radiotherapy apparatus.

Thus, as shown in FIG. 8, the treatment planning computer creates a treatment plan based on knowledge of the desired dose distribution and the individual abilities and constraints of the radiotherapy apparatus 58 in question. This is then passed to the delivery control system 52 of the radiotherapy apparatus 58, which then passes the treatment plan (or at least the relevant parts of it) to individual local control units 54a, 54b, 54c which each control an individual element 56a, 56b, 56c of the radiotherapy apparatus 58. In this case, the individual elements are a collimator leaf drive, the gantry rotation drive, and the dose rate. The local control units 54 then operate the elements 56 and report the current state (such as position) back to the delivery control system 52, which would normally perform all error-checking functions.

An effect of using this method is that the tracking errors during acceleration and deceleration phases will be isolated to the performance of the individual geometry item (or the beam generator). In other words, a divergence between the planned and the actual movement will indicate a component fault or a mis-operation, and will not be an expected result of the component's inertia. This allows tight tolerances to be applied during these phases.

Another effect is that once the step has been profiled, the profiles can be deployed to the local control units responsible for performing the movement and the movement can be executed autonomously. This can therefore be performed over a slow or high latency network, whilst still maintaining high levels of performance. With a distributed control system there is usually a potential for lost communication packets. If the processors that are responsible for the control of a component (axis, dose rate etc) lose packets or are subject to high latency then the performance of the system as a whole will be degraded and become unreliable. According to the invention, however, because they can operate autonomously, the profiles can be transmitted well in advance.

Figure 9:
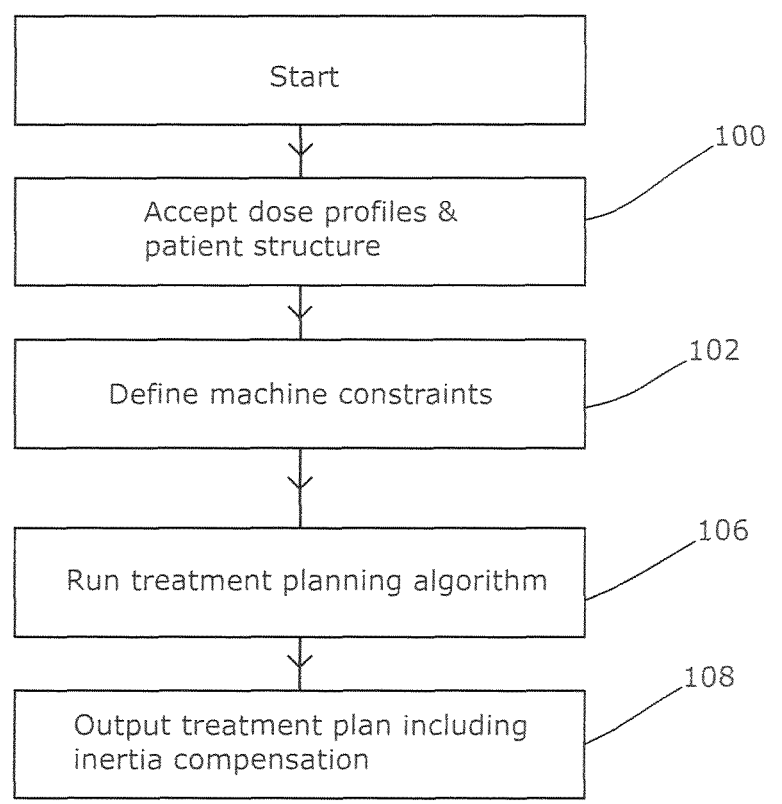
FIG. 9 shows a flowchart for a first embodiment of a treatment planning computer of the present invention.

FIG. 9 shows the process flowchart for the treatment planning computer according to a first embodiment of the present invention. This starts by accepting an intended dose profile 100 which reflects the dose profile that the clinician has prescribed, together with details of the three-dimensional structure of the patient. The latter may be in the form of a segmented CT, MRI or like form of scan, suitably registered to the coordinate system of the dose distribution. Segmentation is a process of marking a CT or MRI scan to indicate the nature of the various tissue types present within the scan, for example bone, soft tissue, tumorous tissue, water, air etc. These different tissue types have different rates of attenuation of x-rays and therefore are taken into account by the treatment planning computer. Registration is a process of aligning the scan so that it employs the same coordinate system as the other aspects of the system, including the dose distribution and the radiotherapy apparatus.

In this embodiment the planning computer will have access to definitions of the machine constraints of the radiotherapy apparatus which will be used to deliver the dose, or these definitions may be provided to it for the planning process (step 102). These set out the nature of the beam which will be used, the range of adjustments that the apparatus can make to the beam (such as the dose rate), the nature of the collimation that is available, the shape of those collimators, and any limits on the movement of those collimators, the maximum speed of the collimator movements and of the gantry rotation, and like information.

The treatment planning computer then performs an algorithmic process based on the required dose distribution and introducing the machine constraints, to yield a detailed treatment plan (step 106). This process is generally known in the art, and may include optimisation processes in which a candidate plan is allowed to evolve iteratively towards a plan that is both deliverable on the apparatus concerned and which delivers the desired dose distribution. That plan is then output (step 108) to the radiotherapy apparatus, after suitable checking by a clinician and/or an automated process.

Figure 10:
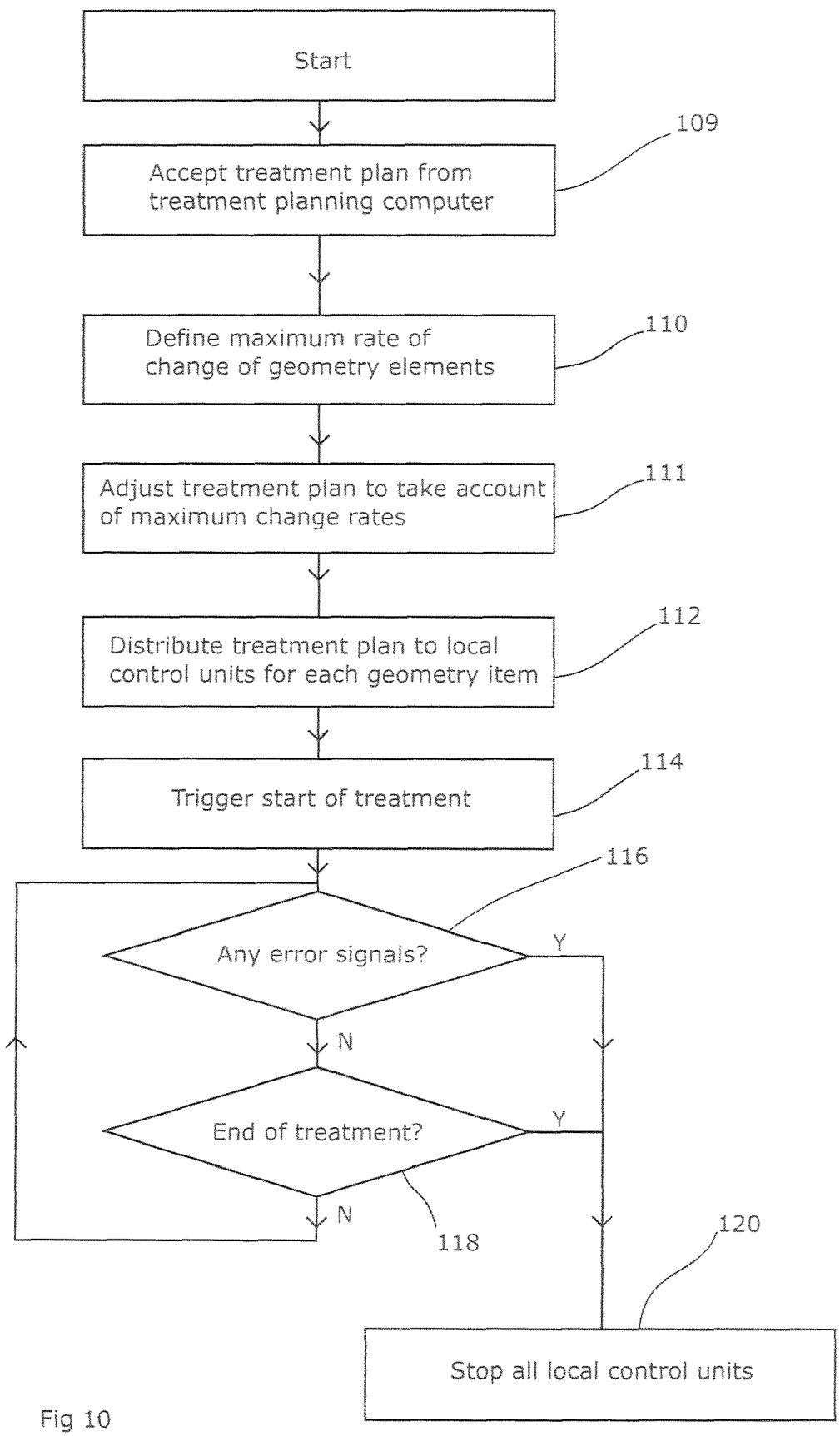
FIG. 10 shows a flowchart for a first embodiment of a delivery control system for a radiotherapy apparatus of the present invention.

FIG. 10 shows the flow chart for the delivery control system 52 of the radiotherapy apparatus. This oversees the apparatus and sends instructions to dedicated local control units 54 that are responsible for individual parts of the apparatus. The delivery control system 52 receives the treatment plan from the treatment planning computer (step 109) and eventually distributes this to the various local control units (step 112). These may each receive either the whole treatment plan, or just the parts of it that are relevant to the part which they control. Once all the local control units have the necessary details and the operator confirms that the patient is ready, the delivery control unit can trigger the start of the treatment (step 114) by sending an appropriate signal to the local control units. From then on, matters can proceed in synchrony with a time signal provided either by an independent clock or by time signal issued from the delivery control unit. The latter only needs to listen for any error states from the local control units (step 116) and send a signal to stop the treatment (step 120) if any are received or if the end of the treatment is reached (step 118).

Prior to distributing the treatment plan to the various local control units (step 112), the delivery control system 52 adjusts the plan to take account of the inertia characteristics of the various elements of the radiotherapy apparatus (step 111). The delivery control system is provided (step 110) with details of the inertia of the various geometry items, i.e. the maximum rate at which their speed and/or their position can be changed. For the gantry, this can be a significant limitation as the rotating gantry structure has a weight of the order of a metric tonne, and thus accelerating it to a desired speed is not a trivial task. Similar considerations apply to the collimator elements; although these are less massive than the gantry, their weight is significant as a result of the use of dense materials such as Tungsten to provide adequate attenuation, and the space available in the rotating head precludes excessively large drive motors. This limitation is provided to the delivery control system 52, which then smoothes the various step changes in the treatment plan so that the slowest-changing element (of those elements that must change at that time), changing as speedily as it can, determines the rate at which the other elements change. Thus the gantry speed, collimator positions, and dose rate all start to change at substantially the same time, and finish changing at substantially the same time. The timings of the various changes can also be adjusted so that the correct total dose is delivered during the segment. This also ensures that the geometry items and the dose rate are adjusted in synchrony, i.e. as shown in FIG. 7, starting to change and finishing their change at substantially the same times.

Figure 11:
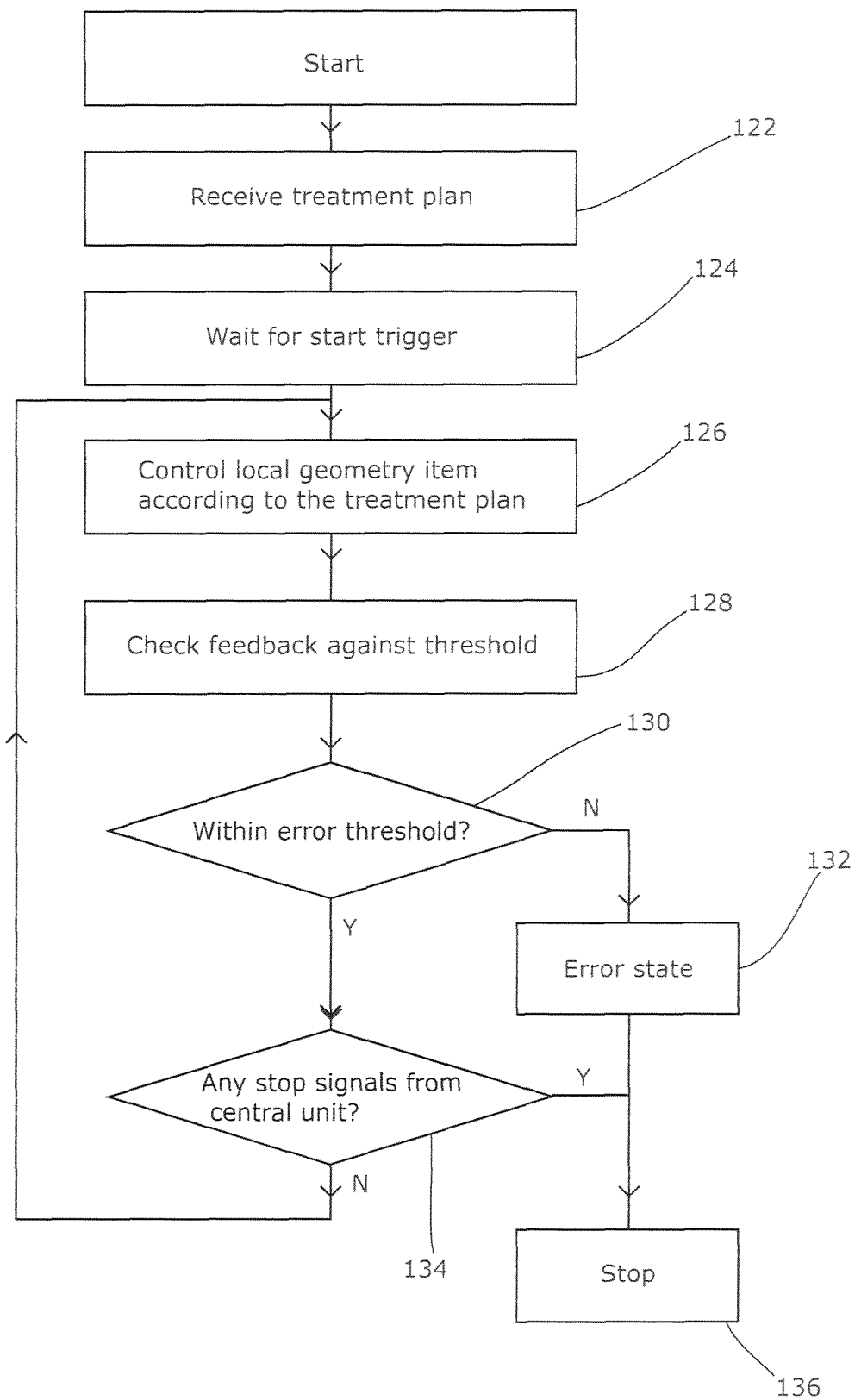
FIG. 11 shows a flowchart for a first embodiment of a local control units for a radiotherapy apparatus of the present invention.

FIG. 11 shows the process adopted by the local control units, responsible for controlling a geometry item of the radiotherapy apparatus. Generally, there will be one such control unit for each item, although the functions of some may be combined into a single unit for closely-related geometry items such as MLC leaves. The unit receives the treatment plan (or at least the parts of the plan relating to it) substantially in its entirety at the start of the treatment (step 122). This plan sets out the required movement of the geometry item in question during the course of the treatment. The unit then waits for the start trigger from the delivery control unit (step 124) and, once that is received, starts working its way through the instructions in the treatment plan (step 126) in synchrony with the clock signal. As a backup, the local control unit may have its own clock to allow it to continue safely if communication with the delivery control unit is lost temporarily.

Whilst controlling the item, the local control unit regularly and (preferably) frequently compares the actual position of the item with the position called for by the treatment plan. This can be compared to an error threshold (step 130) which, importantly, can be set at a relatively low value reflecting only the measurement tolerances for the item's position. No allowance needs to be made for the item's inertia as this will have been taken into account in determining the treatment plan, and therefore the error-checking process for the item in question does not need to bring into consideration the state of any other items (as described above).

If an above-threshold deviation from the plan on the part of the item in question is noticed, then the local control unit enters an error state (step 132) which is communicated back to the delivery control system. If the local control unit enters an error state or receives a stop signal from the overall control unit (step 134), then it stops the process (step 136).

A like control unit is provided for the dose rate.

In this way, the invention creates a revised version of the treatment plan in which the inertia effects of the various elements of the radiotherapy apparatus are catered for, and as a result the treatment plan that is actually put into effect is much more closely achievable, with the advantages set out above. In a second embodiment of the invention, the treatment plan is created ab initio with the inertial effects in mind and therefore need not be revised by the delivery control system.

Figure 12:
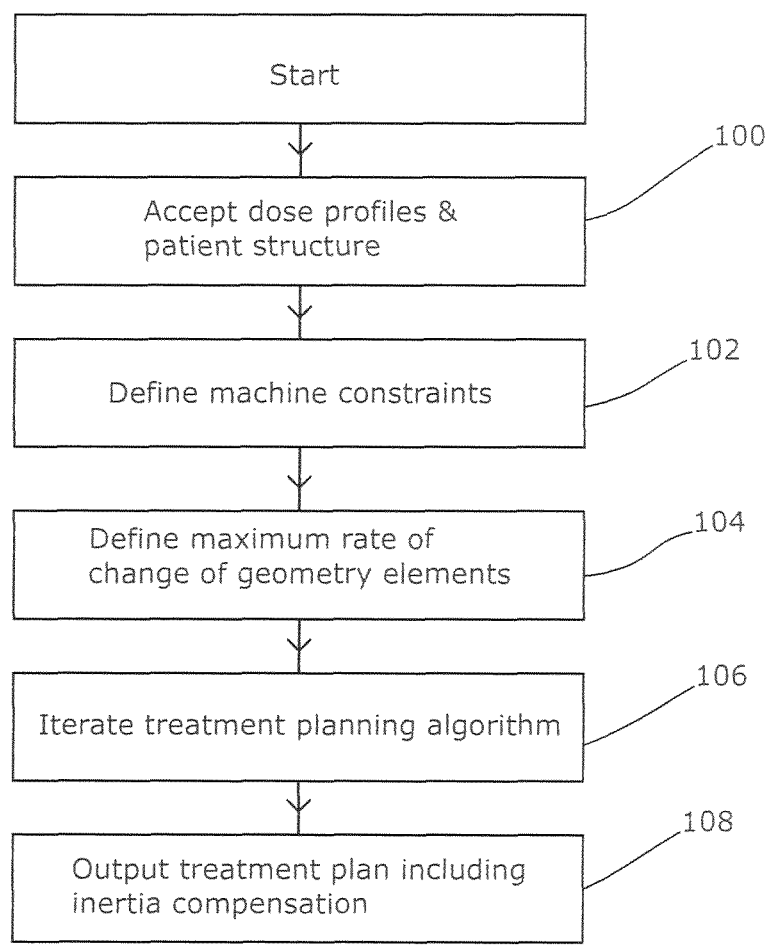
FIG. 12 shows a flowchart for a second embodiment of a treatment planning computer of the present invention.

FIG. 12 shows the process flowchart for the treatment planning computer according to a second embodiment of the present invention. This starts as with the first embodiment, by accepting an intended dose profile 100 which reflects the dose profile that the clinician has prescribed, together with details of the three-dimensional structure of the patient. The latter may be in the form of a segmented CT, MRI or like form of scan, suitably registered to the coordinate system of the dose distribution. In this embodiment, the planning computer again has access to definitions of the machine constraints of the radiotherapy apparatus which will be used to deliver the dose (step 102), but is also provided (step 104) with details of the inertia of the various geometry items, i.e. the maximum rate at which their speed and/or their position can be changed. This limitation is provided to the treatment planning computer as a machine constraint to be taken into account in the planning process. A constraint is also added to require that the geometry items and the dose rate are adjusted in synchrony, i.e. as shown in FIG. 7, starting to change and finishing their change at substantially the same times.

The treatment planning computer then performs the algorithmic process based on the required dose distribution and introducing the machine constraints, to yield a detailed treatment plan (step 106). In this case, the plan will include compensation for the inertia of the various geometry items as this was included within the machine constraints. That plan is then output (step 108) to the radiotherapy apparatus, after suitable checking by a clinician and/or an automated process.

Figure 13:
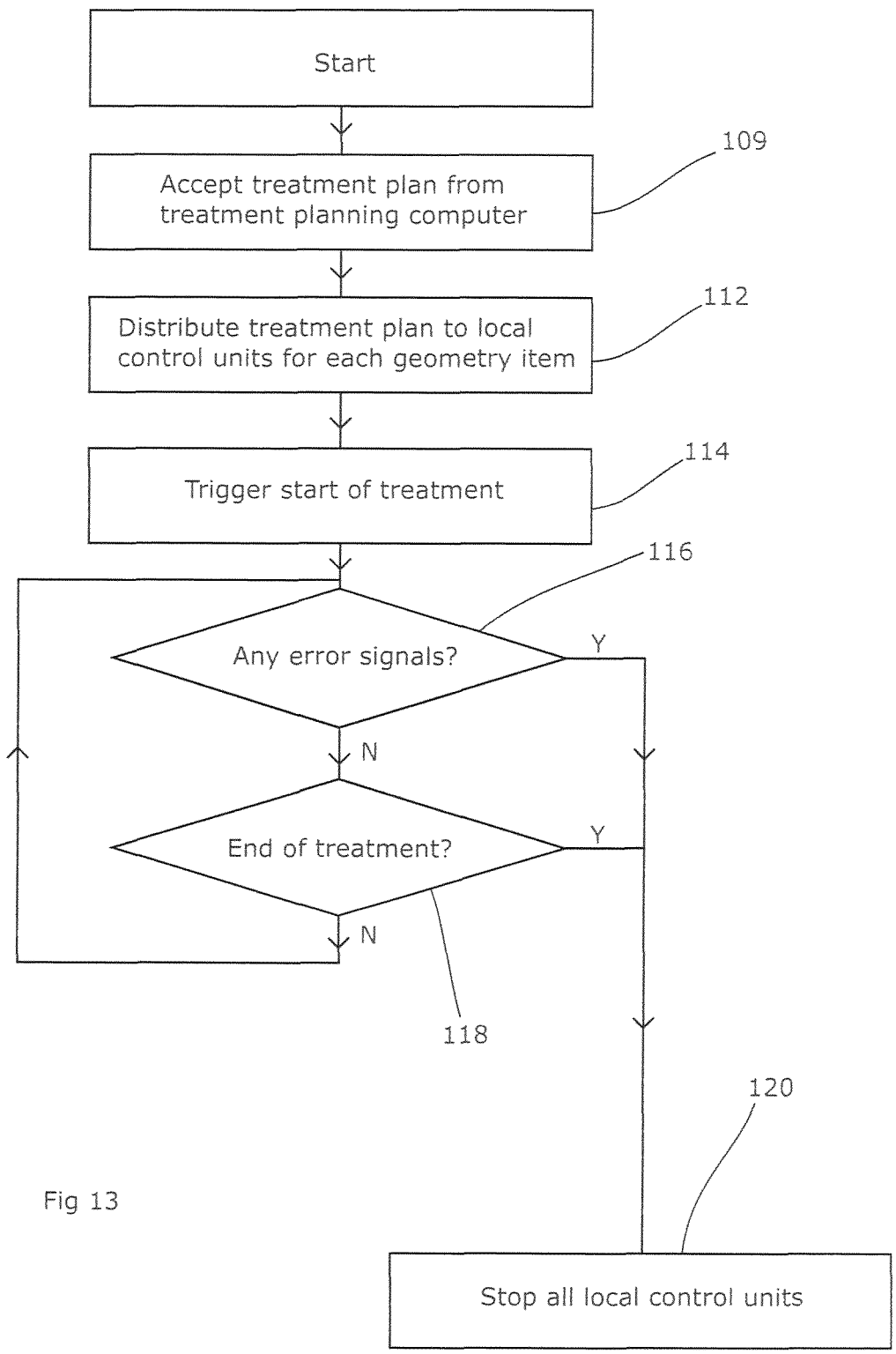
FIG. 13 shows a flowchart for a second embodiment of a delivery control system for a radiotherapy apparatus of the present invention.

FIG. 13 shows the flow chart for the delivery control unit of the radiotherapy apparatus. The delivery control unit receives the treatment plan from the treatment planning computer (step 109) and distributes this to the various local control units (step 112). No revision step is needed as the treatment plan already allows for inertia. Once all the local control units have the necessary details and the operator confirms that the patient is ready, the delivery control unit can trigger the start of the treatment (step 114) by sending an appropriate signal to the local control units. From then on, matters can proceed in synchrony with a time signal provided either by an independent clock or by time signal issued from the delivery control unit. The latter only needs to listen for any error states from the local control units (step 116) and send a signal to stop the treatment (step 120) if any are received or if the end of the treatment is reached (step 118).

The process adopted by the local control units is the same as for the first embodiment, described with reference to FIG. 11. A like control unit is again provided for the dose rate.

In this way, the same end as that of the first embodiment is achieved, but by placing greater constraints on the treatment planning process.

It will of course be understood that many variations may be made to the above-described embodiment without departing from the scope of the present invention.

The invention claimed is:

1. A delivery control system for a radiotherapy apparatus, the delivery control system comprising:
a processor, at least one data store, and a program stored in the data store, wherein the program, when executed by the processor, causes the processor to:
receive a treatment plan;
receive inertial characteristics of a plurality of delivery elements of the radiotherapy apparatus;
produce a delivery plan corresponding to the treatment plan based on the inertial characteristics, wherein the delivery plan matches acceleration or deceleration phases of the plurality of delivery elements so that the plurality of delivery elements move in synchrony during the acceleration phases or during the deceleration phases, wherein the plurality of delivery elements start acceleration or deceleration and stop acceleration or deceleration at substantially the same time; and
transmit at least part of the delivery plan to the plurality of delivery elements.

2. The delivery control system according to claim 1, wherein the program, when executed by the processor, causes the processor to monitor the delivery elements for conformance to the delivery plan.

3. A radiotherapy apparatus, comprising:
a plurality of delivery items, each associated with a local control unit; and a delivery control system including a processor, at least one data store, and a program stored in the data store, wherein the program, when executed by the processor, causes the processor to:
receive a treatment plan;
receive inertial characteristics of the plurality of delivery elements; and
produce a delivery plan corresponding to the treatment plan based on the inertial characteristics, wherein the delivery plan includes a plurality of sequential delivery instructions that match acceleration or deceleration phases of the plurality of delivery elements so that the plurality of delivery elements move in synchrony during the acceleration phases or during the deceleration phases, wherein the plurality of delivery elements start acceleration or deceleration and stop acceleration or deceleration at substantially the same time;
wherein the delivery control system is configured to:
provide the plurality of sequential delivery instructions from the delivery plan to the local control units; and
instruct the local control units to commence a treatment based on the plurality of sequential delivery instructions.

4. The radiotherapy apparatus of claim 3, wherein the local control units are configured to:
receive the plurality of sequential delivery instructions from the delivery control system;
after receiving the instruction to commence the treatment, command movement of a delivery item and monitor subsequent actual movement of the delivery item;
compare the actual movement with movement set out in the plurality of sequential delivery instructions; and
create an alert state if a difference between the actual movement and the movement set out in the plurality of sequential delivery instructions is greater than a threshold.

5. The radiotherapy apparatus according to claim 4, configured to continue the treatment provided that no local control unit is in an alert state.

6. The radiotherapy apparatus of claim 4, wherein the delivery control system is configured to cease the treatment if any local control unit is in an alert state.

7. A radiotherapy apparatus, comprising a plurality of geometry items, each associated with a local control unit, wherein:
the radiotherapy apparatus is configured to:
receive a treatment plan;
receive inertial characteristics of the plurality of geometry items;
produce a plurality of sequential delivery instructions corresponding to the treatment plan based on the inertial characteristics, wherein the plurality of sequential delivery instructions match acceleration or deceleration phases of the plurality of geometry items so that the plurality of geometry items move in synchrony during the acceleration phases or during the deceleration phases, wherein the plurality of geometry items start acceleration or deceleration and stop acceleration or deceleration at substantially the same time; and
provide the plurality of sequential delivery instructions to the local control units and, subsequently, instruct the local control units to commence a treatment.

8. The radiotherapy apparatus of claim 7, wherein the local control units are configured to:
receive the plurality of sequential delivery instructions;
after receiving the instruction to commence treatment, command movement of at least one geometry item and monitor actual movement of the at least one geometry item;
compare the actual movement with movement set out in the plurality of delivery instructions; and
create an alert state if a difference between the actual movement and the movement set out in the plurality of delivery instructions is greater than a threshold.

9. The radiotherapy apparatus according to claim 8, configured to continue the treatment provided that no local control unit is in an alert state.

10. The radiotherapy apparatus of claim 8, configured to cease the treatment if any local control unit is in an alert state.

* * * * *